(12) United States Patent
Xia et al.

(10) Patent No.: US 11,877,793 B2
(45) Date of Patent: Jan. 23, 2024

(54) MEDICAL DEVICES AND RELATED METHODS

(71) Applicant: Boston Scientific Scimed, Inc., Maple Grove, MN (US)

(72) Inventors: Yin Xia, Shanghai (CN); Longsheng Cai, Shanghai (CN); Xinzhe Pei, Shanghai (CN); Minfeng Hua, Shanghai (CN)

(73) Assignee: Boston Scientific Scimed, Inc., Maple Grove, MN (US)

( * ) Notice: Subject to any disclaimer, the term of this patent is extended or adjusted under 35 U.S.C. 154(b) by 259 days.

(21) Appl. No.: 17/123,236

(22) Filed: Dec. 16, 2020

(65) Prior Publication Data

US 2021/0177501 A1 Jun. 17, 2021

(30) Foreign Application Priority Data

Dec. 17, 2019 (CN) .......................... 201911302755.6

(51) Int. Cl.
*A61B 18/14* (2006.01)
*A61B 18/00* (2006.01)

(52) U.S. Cl.
CPC ...... *A61B 18/1477* (2013.01); *A61B 2018/00083* (2013.01); *A61B 2018/00136* (2013.01); *A61B 2218/002* (2013.01)

(58) Field of Classification Search
CPC .. A61B 2018/1477; A61B 2018/00083; A61B 2018/00136; A61B 2218/002
See application file for complete search history.

(56) References Cited

U.S. PATENT DOCUMENTS

| | | | | |
|---|---|---|---|---|
| 7,371,236 | B2 * | 5/2008 | Okada | A61B 18/1402 606/45 |
| 7,632,266 | B2 * | 12/2009 | Scopton | A61B 18/1482 606/49 |
| 2003/0225401 | A1 * | 12/2003 | Eggers | A61B 18/148 606/39 |
| 2005/0090816 | A1 * | 4/2005 | McClurken | A61B 17/32 606/49 |
| 2009/0254085 | A1 | 10/2009 | Yamamoto | |
| 2016/0220301 | A1 * | 8/2016 | Yamamoto | A61B 18/14 |
| 2019/0298435 | A1 * | 10/2019 | Estevez | A61B 18/14 |
| 2020/0060756 | A1 | 2/2020 | Smith et al. | |

FOREIGN PATENT DOCUMENTS

WO  WO 2005079901  9/2005

OTHER PUBLICATIONS

International Search Report and Written Opinion issued in International Application No. PCT/US2020/065201, dated Mar. 17, 2021 (13 pages).

* cited by examiner

*Primary Examiner* — Linda C Dvorak
*Assistant Examiner* — Abigail Bock
(74) *Attorney, Agent, or Firm* — Bookoff McAndrews, PLLC (57) ABSTRACT

A medical device includes an electrode shaft and an insulation tip. The electrode shaft is configured to deliver energy to a target site and includes an electrode shaft lumen configured to deliver fluid to the target site. The insulation tip is coupled to a distal tip of the electrode shaft. The insulation tip includes an insulation tip lumen fluidly connected to the electrode shaft lumen and configured to deliver fluid to the target site. The insulation tip covers an entirety of the distal tip of the electrode shaft.

20 Claims, 4 Drawing Sheets

MEDICAL DEVICES AND RELATED METHODS

CROSS-REFERENCE TO RELATED APPLICATION(S)

This application claims the benefit of priority from Chinese Patent Application No. 201911302755.6, filed on Dec. 17, 2019, which is incorporated by reference herein in its entirety.

TECHNICAL FIELD

Aspects of the present disclosure generally relate to medical devices and related methods. In particular, aspects of the present disclosure relate to medical devices and related methods configured for the treatment of tissue by delivering electrical energy to or into tissue and/or injecting fluid into and/or under tissue with an electrode having an insulated distal tip.

BACKGROUND

Medical devices, such as endoscopes or other suitable insertion devices, are employed for a variety of types of diagnostic and surgical procedures, such as endoscopy, laparoscopy, arthroscopy, gynoscopy, thoracoscopy, cystoscopy, etc. Many of these procedures involve delivering energy to tissue of an organ or a gland to treat tumors, infections, and the like. Examples of such procedures include Endoscopic Mucosal Resection (EMR), Endoscopic Sub-mucosal Resection (ESR), Endoscopic Sub-mucosal Dissection (ESD), polypectomy, mucosectomy, etc. In particular, such procedures may be carried out by inserting an insertion device into a subject's body through a surgical incision, or via a natural anatomical orifice (e.g., mouth, vagina, or rectum), and performing the procedure or operation at a target site with an auxiliary device inserted through the insertion device.

At times, during a medical procedure, a user may use an injection needle and an energy delivery device for purposes of raising, separating, flushing, cutting, dissecting, ablating, marking, coagulating, cauterizing, or otherwise treating and/or manipulating tissue. The injection and energy delivery may be performed separately. For example, in order to deliver energy to the tissue, the user may be required to remove the injection needle from the insertion device and deliver the energy delivery device through the insertion device to the tissue being targeted, and vice versa. During the procedure, the user may alternate using the injection needle and the energy delivery device, and exchanging devices may increase the duration and risks of the medical procedure. Additionally, one or more portions of the energy delivery device may inadvertently contact or harm tissue (or an inner channel of the insertion device) when energized.

The devices and methods of the current disclosure may rectify one or more of the deficiencies described above or address other aspects of the art.

SUMMARY

Examples of the present disclosure relate to, among other things, medical devices configured for treating tissue by delivering electrical energy to the tissue, and configured for delivering fluid into and/or under the tissue. Each of the examples disclosed herein may include one or more of the features described in connection with any of the other disclosed examples.

In one example, a medical device may include an electrode shaft and an insulation tip. The electrode shaft may be configured to deliver energy to a target site and may include an electrode shaft lumen configured to deliver fluid to the target site. The insulation tip may be coupled to a distal tip of the electrode shaft. The insulation tip may include an insulation tip lumen fluidly connected to the electrode shaft lumen and may be configured to deliver fluid to the target site. The insulation tip may cover an entirety of the distal tip of the electrode shaft.

The medical device may include one or more of the following features. The insulation tip may include a rounded distal end and a cylindrical side portion. The rounded distal end may be hemispherical and may extend distally beyond the distal tip of the electrode shaft. The insulation tip lumen may include a wide portion configured to receive a portion of the distal tip of the electrode shaft and a narrow portion extending distally beyond the distal tip of the electrode shaft. The narrow portion of the insulation tip lumen may include a cross-sectional width equal to a cross-sectional width of the electrode shaft lumen, and the narrow portion may include a chamfered distal end portion. The electrode shaft lumen and the insulation tip lumen may extend along a longitudinal axis of the medical device.

The insulation tip may be coupled to the electrode shaft via solder. A radially interior portion of the insulation tip may include a gap configured to receive at least a portion of the solder. The insulation tip may be coupled to the electrode shaft via brazing. When the insulation tip is coupled to the electrode shaft, a filler material may occupy a space at a junction between a portion of the electrode shaft and a portion of the insulation tip.

The insulation tip may include two insulation tip halves that are coupled together to couple the insulation tip to the electrode shaft. The electrode shaft may include a widened distal portion. Each of the two insulation tip halves may include a groove to receive at least a portion of the widened distal portion when the insulation tip halves are coupled to the electrode shaft. The groove in each of the two insulation tip halves may be positioned between the wide portion of the insulation tip lumen configured to receive the portion of the distal tip of the electrode shaft and the narrow portion of the insulation tip lumen extending distally beyond the distal tip of the electrode shaft.

The electrode shaft may include a first longitudinal portion, a second longitudinal portion proximal of the first longitudinal portion, and a transition portion between the first longitudinal portion and the second longitudinal portion. The first longitudinal portion may include a cross-sectional width less than a cross-sectional width of the second longitudinal portion. The electrode shaft may be formed of stainless steel, and the insulation tip may be formed of a ceramic or polymer material.

In another example, a medical device may include a handle including a fluid port and an energy receiving hub. The medical device may also include a shaft including a shaft lumen configured to direct a flow of fluid through the shaft from the fluid port. The medical device may also include a conductive element and an electrode. The conductive element may be electrically connected to the energy receiving hub and may pass through at least a portion of the handle and/or the shaft. The electrode may be coupled to a distal end of the shaft and include an electrode shaft and an insulation tip coupled to a distal tip of the electrode shaft.

The electrode shaft may be electrically connected to the conductive element and may include an electrode shaft lumen fluidly connected to the shaft lumen. The insulation tip may include an insulation tip lumen fluidly connected to the electrode shaft lumen and may be configured to deliver fluid from a distal end of the electrode. The insulation tip may cover an entirety of the distal tip of the electrode shaft.

The medical device may include one or more of the following features. The handle may further include a main body and a movable body. Movement of the movable body relative to the main body may move the electrode relative to the distal end of the shaft. With the movable body in a proximally retracted position, only the insulation tip may be exposed distally beyond the shaft. With the movable body in a distally extended position, the insulation tip and at least a portion of the electrode shaft may be exposed distally beyond the shaft.

In yet another example, a medical device may include an electrode shaft and an insulation tip. The electrode shaft may include an electrode shaft lumen configured to receive fluid. The insulation tip may be coupled to a distal tip of the electrode shaft. The insulation tip may include a rounded distal portion that extends distally beyond the electrode shaft. The insulation tip may include an insulation tip lumen fluidly connected to the electrode shaft lumen to form a channel. The channel may extend along a longitudinal axis of the medical device.

The medical device may include one or more of the following features. The insulation tip may be coupled to the electrode shaft by soldering or brazing. The insulation tip may include two insulation tip halves that are coupled together to couple the insulation tip to the electrode shaft. The electrode shaft may include a widened distal portion, and each of the two insulation tip halves may include a groove to receive at least a portion of the widened distal portion when the insulation tip halves are coupled to the electrode shaft.

It may be understood that both the foregoing general description and the following detailed description are exemplary and explanatory only and are not restrictive of the disclosure, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

FIG. 1A illustrates an exemplary medical device.

FIG. 2A illustrates a side view of an electrode portion of the medical device of FIGS. 1A and 1B.

FIG. 3A illustrates a side view of an alternative exemplary electrode portion of the medical device of FIGS. 1A and 1B.

DETAILED DESCRIPTION

Examples of the present disclosure include devices and methods for: facilitating and improving the efficacy, efficiency, and safety of treating and/or manipulating tissue when, for example, applying electrical energy to tissue with an electrode; delivering fluid into and/or under tissue during a medical procedure through the distal end of the electrode; and insulating a distal tip of the electrode. For example, aspects of the present disclosure may provide a user (e.g., physician, medical technician, or other medical service provider) with the ability to apply electrical energy or heat to tissue using a medical device having an electrode, and to deliver fluid into and/or under tissue with the same medical device. Aspects of the present disclosure may provide the user with the ability to apply electrical energy or heat and deliver fluid with a reduced likelihood of damaging tissue or contacting unintended portions of the tissue. Some aspects of the present disclosure may be used in performing an endoscopic, laparoscopic, arthroscopic, gynoscopic, thoracoscopic, cystoscopic, or other type of procedure.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device. When used herein, "proximal" refers to a position relatively closer to the exterior of the body of a subject or closer to a user, such as a medical professional, holding or otherwise using the medical device. In contrast, "distal" refers to a position relatively further away from the medical professional or other user holding or otherwise using the medical device, or closer to the interior of the subject's body. As used herein, the terms "comprises," "comprising," "having," "including," or other variations thereof, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." As used herein, the terms "about," "substantially," and "approximately," indicate a range of values within +/−10% of a stated value.

Figure 1A:
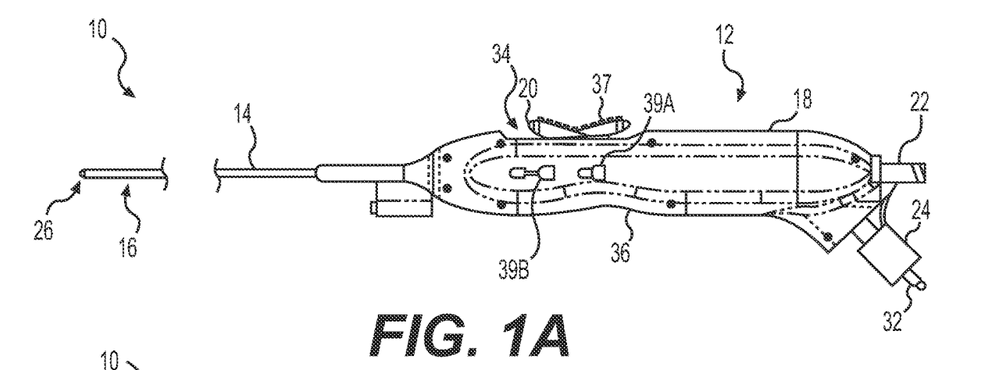
Figure 1B:
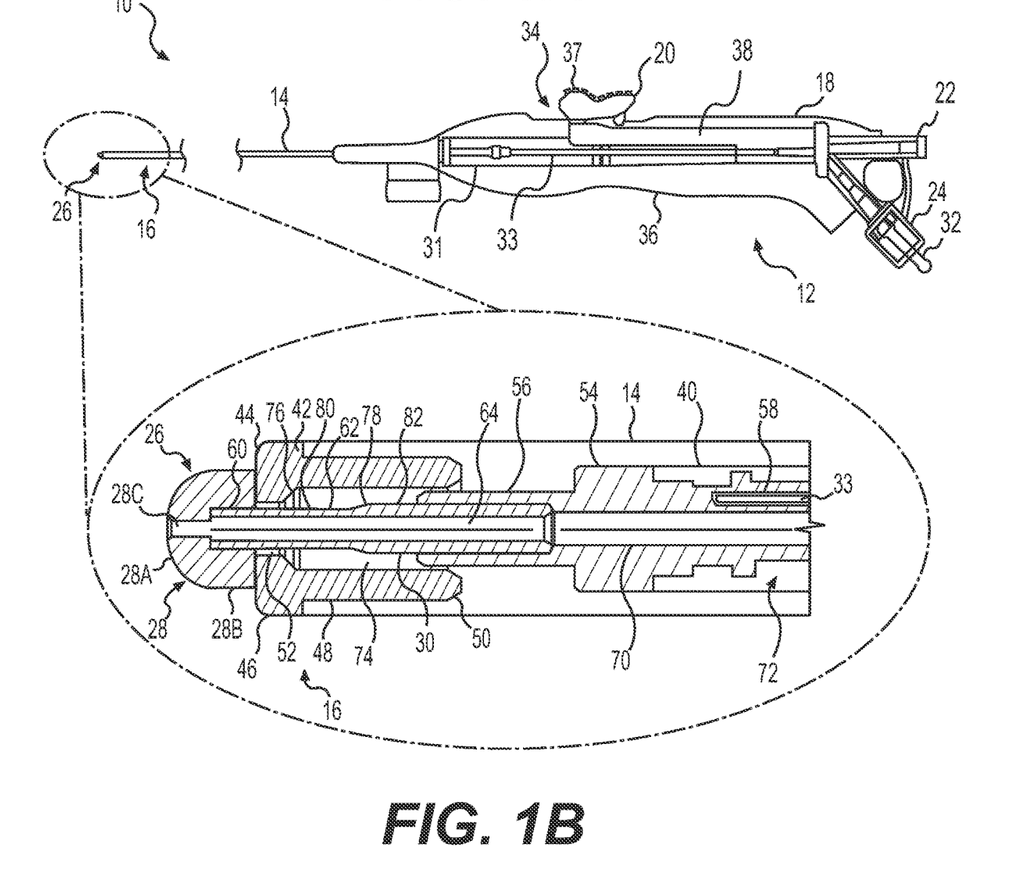
FIG. 1B illustrates a cross-sectional view of the medical device with a distal portion of the medical device enlarged, according to aspects of this disclosure.

FIGS. 1A and 1B depict a medical device 10 that includes a handle 12, a shaft 14, and a distal end 16. Handle 12 may include a main body 18 and a movable body 20. Handle 12 also may include a port 22 configured to receive fluid, and a hub 24 configured to receive electrical energy similar to an electrical plug or socket. Distal end 16 includes an end effector, for example, an electrode portion 26 (hereinafter "electrode 26"). Electrode 26 is electrically connected to hub 24, and as discussed in detail below, may include a channel fluidly connected to, or otherwise in fluid communication with, port 22. Additionally, as shown in FIG. 1B and discussed in detail below, electrode 26 may include an insulation tip 28, which may at least partially surround a distal portion of an electrode shaft 30.

Medical device 10 may be inserted into a body lumen of a subject, either through an insertion device (not shown) or alone, such that at least a portion of shaft 14 may be within the subject, while handle 12 may remain outside of the subject. Distal end 16 may be positioned at a target site within the subject. From outside of the subject, a user can manipulate handle 12. Movement of movable body 20 relative to main body 18 in a first direction (e.g., the distal direction) may extend electrode 26 relative to shaft 14 (e.g., move electrode 26 distally relative to a distal end of shaft 14), while movement of movable body 20 relative to main body 18 in a second direction (e.g., the proximal direction) may retract electrode 26 relative to shaft 14 (e.g., move electrode 26 proximally relative to a distal end of shaft 14). Although not shown, movable body 20 or additional components of handle 12 may articulate electrode 26 (or electrode 26 and distal end 16) left or right, and/or up or down relative to shaft 14.

Handle 12 may be coupled to a fluid source (not shown) via port 22. Port 22 may be in fluid communication with electrode 26 via an internal lumen 31, which may extend through handle 12 (FIG. 1B) and shaft 14. It is noted that various portions of handle 12 shown in FIG. 1B may not be to scale, in order to more fully illustrate various portions of handle 12. In one aspect, internal lumen 31 may extend longitudinally through main body 18 of handle 12 and shaft 14 to fluidly connect port 22 to electrode 26. Port 22 may be positioned on a proximal portion of main body 18, for example, a proximal end of main body 18. Alternatively, port 22 may be positioned on a distal or central portion of main body 18. Moreover, port 22 may include a one-way valve, a luer, a seal, threading, and/or any appropriate element to help maintain a secure connection between handle 12 and the fluid source, minimize or prevent backflow (e.g., fluid flowing proximally out of port 22), and/or minimize or prevent leakage. In one example, a one-way valve may include an outer housing containing an inner elastomeric and/or gelatinous sealing member (not shown).

Handle 12 may be coupled to an energy source (not shown) through hub 24. Hub 24 may include one or more prongs or pins 32 to couple to the energy source. Hub 24 may be electrically coupled to electrode 26 via a conductive element 33, which may be electrically coupled to pin 32 and extend through handle 12 and through at least a portion of shaft 14. The energy source may be an electrocautery source, a radio frequency generator, a heating source, a current generator, etc. In one aspect, medical device 10 may be used for monopolar electrosurgery, and may include a return electrode positioned remotely from electrode 26 on or otherwise adjacent the subject. In another aspect, medical device 10 may be used for bipolar electrosurgery. In that instance, electrode 26 may include an active electrode portion, and a return electrode may be provided at or near another portion of electrode 26 and/or shaft 14. In one example, although not shown, two conductive elements may run through shaft 14, where the conductive elements may be electrically isolated from each other, allowing one to conduct energy to the active electrode and the other to conduct energy from a return electrode.

Hub 24 may be positioned on main body 18, for example, on a proximal end of main body 18. In one aspect, port 22 may extend from the proximal end of main body 18 in a direction parallel to a longitudinal axis of main body 18, and hub 24 may extend from the proximal end of main body 18 at an angle transverse (e.g., approximately 45 degrees) to the longitudinal axis of main body 18. In another aspect, hub 24 may be positioned on a distal or central portion of main body 18, or on movable body 20. Although not shown, main body 18 and/or hub 24 may include a one-way valve, a luer, a seal, threading, and/or any appropriate element to help maintain a secure connection between handle 12 and the energy source, minimize or prevent back-flow (e.g., fluid flowing from port 22 and/or internal lumen 31 and proximally out of hub 24), and/or minimize or prevent leakage.

In one aspect shown in FIG. 1B, pin 32 may extend through hub 24 transverse to a longitudinal axis of handle 12, and may be electrically and physically connected to conductive element 33, such as a wire, a cable, and/or a braided sheath. Conductive element 33 may be electrically conductive or include an electrically conductive element, and conductive element 33 may extend longitudinally through internal lumen 31 and through shaft 14. As shown in FIG. 1B, fluid delivered through port 22 may surround at least a portion of conductive element 33. In one aspect, conductive element 33 may include one or more layers of insulation to help insulate conductive element 33 from the fluid in internal lumen 31. As alluded to above, a second conductive element (not shown) may be provided as a return pathway where medical device 10 has a bipolar configuration. Although not shown, in another aspect, the energy source may be a part of handle 12 (e.g., an internal battery in handle 12).

As mentioned, handle 12 may control the extension or retraction of electrode 26 relative to the distal end 16 of shaft 14. For example, main body 18 may include a slot 34, and movable body 20 may be slidably positioned within slot 34. For example, main body 18 may be configured to be held by a user's hand, and movable body 20 may be configured to be controlled by the movement of the user's thumb. For example, a side of main body 18 opposite to movable body 20 may include one or more contours 36, which may help the user grip main body 18. Additionally, movable body 20 may include one or more ridges 37, which may help the user manipulate movable body 20. Movable body 20 may be lockable in one or more positions relative to main body 18, and/or may be spring-biased in a direction (e.g., toward a proximally retracted position).

Movable body 20 may be coupled to a drive element, and the drive element may impart distal or proximal movement to at least a portion of electrode 26 based on relative movement between main body 18 and movable body 20. In one aspect, conductive element 33 may also act as a drive wire, rod, cable, or the like, such that conductive element 33 imparts distal or proximal movement to at least a portion of electrode 26 while also coupling electrode 26 to hub 24, e.g., the one or more pins 32, to deliver the energy to (and/or from) electrode 26. As shown in FIG. 1B, movable body 20 may be coupled to conductive element 33 via a coupling mechanism, for example, a coupler 38. In one aspect, coupler 38 may be physically coupled (either directly or indirectly) to movable body 20, and may also be physically coupled (either directly or indirectly) to conductive element 33 such that movement of movable body 20 extends or retracts conductive element 33, and thus extends or retracts electrode 26. It is noted that coupler 38 and/or other components within handle 12 may help maintain the electrical connection between pin 32 and conductive element 33 when conductive element 33, and thus electrode 26, is in the retracted or extended positions. Alternatively, in another aspect, coupler 38 and/or other components within handle 12 may be configured to only electrically connect pin 32 and conductive element 33 when conductive element 33, and thus electrode 26, is in the extended position, or an at least partially extended position.

As shown in FIG. 1A, handle 12 may also include one or more indicators, for example, indicators 39A, 39B. For example, indicators 39A, 39B may visually indicate to the user the position of electrode 26 relative to shaft 14. The position of indicators 39A, 39B may also correspond with the position of movable body 20. For example, indicator 39A may be positioned on handle 12 at a position corresponding with a retracted position of movable body 20, and may indicate that electrode 26 is retracted relative to shaft 14. Similarly, indicator 39B may be positioned on handle 12 at a position corresponding with an extended position of movable body 20, and may indicate that electrode 26 is extended relative to shaft 14.

As shown in FIGS. 1A and 1B, shaft 14 extends from a distal portion of main body 18 to distal end 16, and may surround at least a portion of electrode 26. Shaft 14 may be a sheath that surrounds at least a portion of one or more lumens (e.g., lumen 31) and the drive wire (e.g., conductive element 33). In another aspect, shaft 14 may be an extrusion that includes one or more lumens extending from handle 12 to distal end 16.

The enlarged portion of FIG. 1B illustrates additional features of shaft 14 and distal end 16. Electrode 26 includes insulation tip 28 surrounding a distal portion of electrode shaft 30. Electrode 26 may be positioned within a portion of an end cap 42 of distal end 16. End cap 42 may include a distal end face 44 and graduated surfaces 46, 48, and 50. For example, a first graduated surface 46 may be at a distalmost portion of end cap 42. As shown in FIG. 1B, with shaft 14 coupled to distal end 16, first graduated surface 46 of end cap 42 may be exposed distally beyond shaft 14, while a second graduated surface 48 may be received in shaft 14. A third graduated surface 50 may, for example, be tapered to facilitate insertion of end cap 42 into shaft 14. In another example, shaft 14 may fully enclose the radially exterior portions of end cap 42. End cap 42 may be at least partially electrically insulating. For example, end cap 42 may be formed of a ceramic material or another non-conductive material. Alternatively, only distal end face 44 and an internal portion of end cap 42 that contacts and/or surrounds electrode 26 may be electrically insulating. Distal end face 44 includes a central opening 52 through which electrode 26 may extend and retract.

Electrode 26 may be coupled to a proximal support 54 of distal end 16, which may include a cylindrical extension 56. Proximal support 54 may be coupled to a portion of the drive wire (e.g., conductive element 33) via a drive wire receiving portion 58. Cylindrical extension 56 may extend distally and may receive at least a portion of electrode 26. Electrode 26 and cylindrical extension 56 may be coupled via welding, an adhesive, crimping, friction fit, or other appropriate coupling. In one aspect, cylindrical extension 56 may allow for different electrodes 26 to be removably coupled to distal end 16. Proximal support 54 includes a support lumen 70, and support lumen 70 fluidly connects port 22 to electrode 26, for example, via a lumen (e.g., lumen 31) through shaft 14.

Proximal support 54 includes a proximal coupling portion 72, which includes drive wire receiving portion 58. Drive wire receiving portion 58 may be an indentation that extends parallel to at least a portion of support lumen 70. Drive wire receiving portion 58 may receive a portion of a drive wire (not shown), and the drive wire and/or an inner sheath 40 may be coupled to movable body 20 such that the movement of movable body 20 imparts distal or proximal movement to proximal support 54 and, thus, to electrode 26. The drive wire may be coupled to drive wire receiving portion 58 within coupling portion 72 by welding, an adhesive, crimping, friction fit, or any other permanent or temporary coupling. Proximal support 54 may also be coupled to electrode 26 by welding, an adhesive, crimping, friction fit, or any other permanent or temporary coupling. In one aspect, both the drive wire and proximal support 54 are conductive to electrically connect the one or more prongs 32 of hub 24 to electrode 26. In another aspect, proximal support 54 may be at least partially insulating, and may include a wire or other conductive element electrically connecting the drive wire to electrode 26. Similarly, in one aspect, the drive wire may be at least partially insulating and may include a wire or other conductive element. Furthermore, at least a portion of the drive wire may be positioned within inner sheath 40. Alternatively, the drive wire may be positioned within a separate lumen in shaft 14 (e.g., a lumen separate from the lumen running through inner sheath 40).

End cap 42 includes a central portion 74 through which electrode shaft 30 may move during the extension and retraction. End cap 42 may also include a narrowing portion or stop surface 76 at a distal end of central portion 74. Electrode shaft 30 may include a transition portion 78 between a first longitudinal portion 80 and a second longitudinal portion 82. Stop surface 76 and transition portion 78 may limit the distal extension of electrode 26 through end cap 42. In a fully extended position, first longitudinal portion 80 may protrude from end cap 42 and may form an exposed portion that may be used for cutting or otherwise treating tissue. Additionally, although not shown, end cap 42 may be fixedly coupled to shaft 14 via welding, an adhesive, crimping, friction fit, or other appropriate coupling.

Electrode 26 and proximal support 54 may be movable relative to end cap 42 in response to the relative movement of movable body 20 and main body 18 of handle 12. For example, with movable body 20 in a proximal position relative to main body 18, electrode shaft 30 may be substantially retracted within end cap 42 with only a distal portion of electrode 26 (e.g., insulation tip 28) extending distally beyond end cap 42. Then, as movable body 20 is translated distally relative to main body 18, electrode 26 and proximal support 54 translate distally relative to end cap 42 such that a greater portion of electrode 26 (e.g., electrode shaft 30) extends distally beyond end cap 42 through central opening 52.

Alternatively, although not shown, central opening 52 may be larger than insulation tip 28, and with movable body 20 in the proximalmost position, electrode 26 (including insulation tip 28) may be fully retracted within central opening 52 of end cap 42. Furthermore, in one aspect, movable member 20 may have an equilibrium position relative to main body 18, and the equilibrium position may correspond to electrode shaft 30 being partially extended from end cap 42.

As shown in the enlarged portion of FIG. 1B, electrode shaft 30 includes a distal tip 60 and a longitudinal portion 62. Distal tip 60 and longitudinal portion 62 may be formed by first longitudinal portion 80. Distal tip 60 may be received within insulation tip 28 and covered by insulation tip 28, and longitudinal portion 62 may be proximal to insulation tip 28 and not covered by insulation tip 28.

Electrode shaft 30 also includes an electrode shaft lumen 64 extending through electrode shaft 30, for example, extending longitudinally through a central portion of electrode shaft 30. Electrode shaft lumen 64 may be in fluid communication with port 22 via support lumen 70 through proximal support 54. In one aspect, inner sheath 40 may form at least a portion of the fluid connection between lumen 70 and port 22. Additionally, electrode shaft lumen 64 is in fluid communication with an insulation tip lumen 28C to form a channel to deliver fluid from a distal end of electrode 26.

As shown in FIG. 1B, insulation tip 28 may include a distal end 28A and a side portion 28B. Distal end 28A may be rounded, for example, substantially hemispherical, and side portion 28B may include straight sides, for example, may be substantially cylindrical. In one aspect, the shapes of distal end 28A and side portion 28B may help distal end 16 be atraumatic, and/or may help abut, position, manipulate, or otherwise treat tissue, while electrode 30 may be used to cut, dissect, ablate, mark, coagulate, cauterize, or otherwise treat tissue. Nevertheless, this disclosure is not so limited, and insulation tip 28, including distal end 28A and side portion 28B, may include other shapes. For example, insulation tip 28 may be frustoconical, tapered, chamfered, filleted, beveled, or combinations thereof. In one aspect, insulation tip 28 completely surrounds or covers a distal portion (e.g. distal tip 60) of electrode shaft 30. For example, insulation tip 28 may cover approximately one quarter of a length of first longitudinal portion 80 of electrode shaft 30. In another example, insulation tip 28 may cover approximately one third or one half of the length of first longitudinal portion 80 of electrode shaft 30. In this aspect, insulation tip 28 may provide an insulation from the distal portion of electrode shaft 30 and at least a portion of the tissue near insulation tip 28. For example, insulation tip 28 may abut tissue, and electrode shaft 30 may be energized while insulation tip 28 helps to insulate the tissue that insulation tip 28 abuts against. Moreover, insulation tip 28 may receive distal tip 60 within approximately one half of insulation tip 28 along the longitudinal axis, which may help securely couple insulation tip 28 and electrode 30. Additionally, approximately one half of insulation tip 28 may extend distally beyond distal tip 60, which may help insulate tissue abutting distal position 28A of insulation tip 28 when electrode 30 is energized.

As discussed below, insulation tip 28 and electrode shaft 30 may be physically coupled, for example, via one or more of soldering, brazing, welding, bonding, or one or more other coupling mechanisms. Moreover, insulation tip 28 and electrode shaft 30 form a fluid channel that extends through both electrode shaft 30 and insulation tip 28 in order to deliver (e.g., inject) fluid to a target site (e.g., within or between layers of tissue to raise, separate, flush, or otherwise treat tissue). Electrode shaft 30 may be energized, and the exposed portion of electrode shaft 30 (e.g., longitudinal portion 62) may be used to cut, dissect, ablate, mark, coagulate, cauterize, or otherwise treat tissue.

Figure 2A:
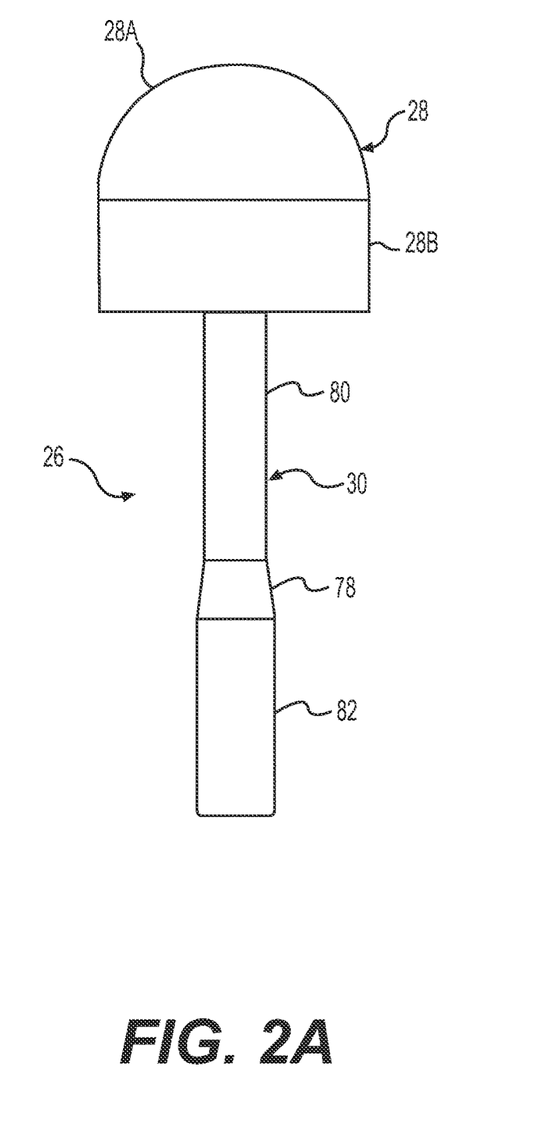
Figure 2B:
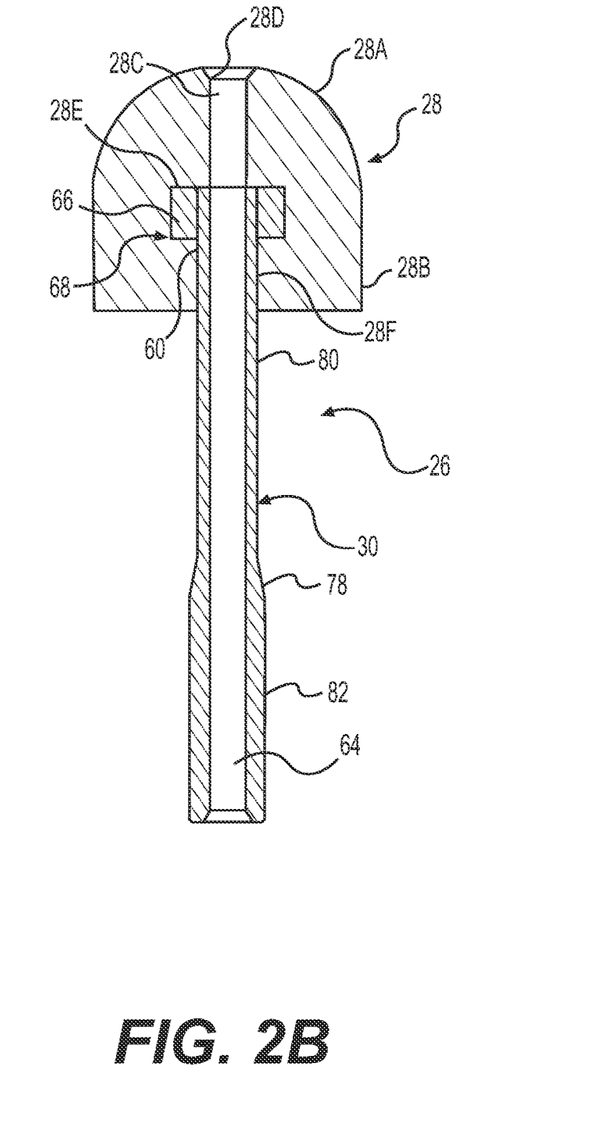
FIG. 2B illustrates a cross-sectional view of the electrode portion of FIG. 2A, according to aspects of the present disclosure.

FIGS. 2A and 2B illustrate additional aspects of electrode 26 that may form a portion of distal end 16 of medical device 10. FIG. 2A shows a side view of electrode 26, and FIG. 2B shows a cross-sectional view of electrode 26. As mentioned, electrode 26 includes insulation tip 28 surrounding electrode shaft 30. Insulation tip 28 may include distal portion 28A and side portion 28B. As shown in FIGS. 1B and 2B, insulation tip 28 includes insulation tip lumen 28C. In this aspect, fluid delivered through electrode shaft lumen 64 may be delivered distally through insulation tip lumen 28C. In one aspect, electrode shaft lumen 64 and insulation tip lumen 28C may be approximately the same size. In another aspect, electrode shaft lumen 64 and insulation tip lumen 28C may be tapered distally such that distal portions of the lumens are narrower than proximal portions of the lumens. Alternatively, electrode shaft lumen 64 and insulation tip lumen 28C may be tapered proximally such that proximal portions of the lumens are narrower than distal portions of the lumens. In these aspects, varying sizes of electrode shaft lumen 64 and insulation tip lumen 28C may help increase or decrease the pressure of the fluid being delivered through the fluid channel. A distal end portion 28D of insulation tip lumen 28C may include a chamfer or angled portion, which may help disperse, direct, or otherwise deliver fluid to a target site with a decreased likelihood of damaging tissue. Additionally, distal end 28A of insulation tip 28 may include an internal face 28E. When insulation tip 28 and electrode 30 are coupled together, the distal end face of electrode 20 may abut internal face 28E.

Figures 4A, 4B:
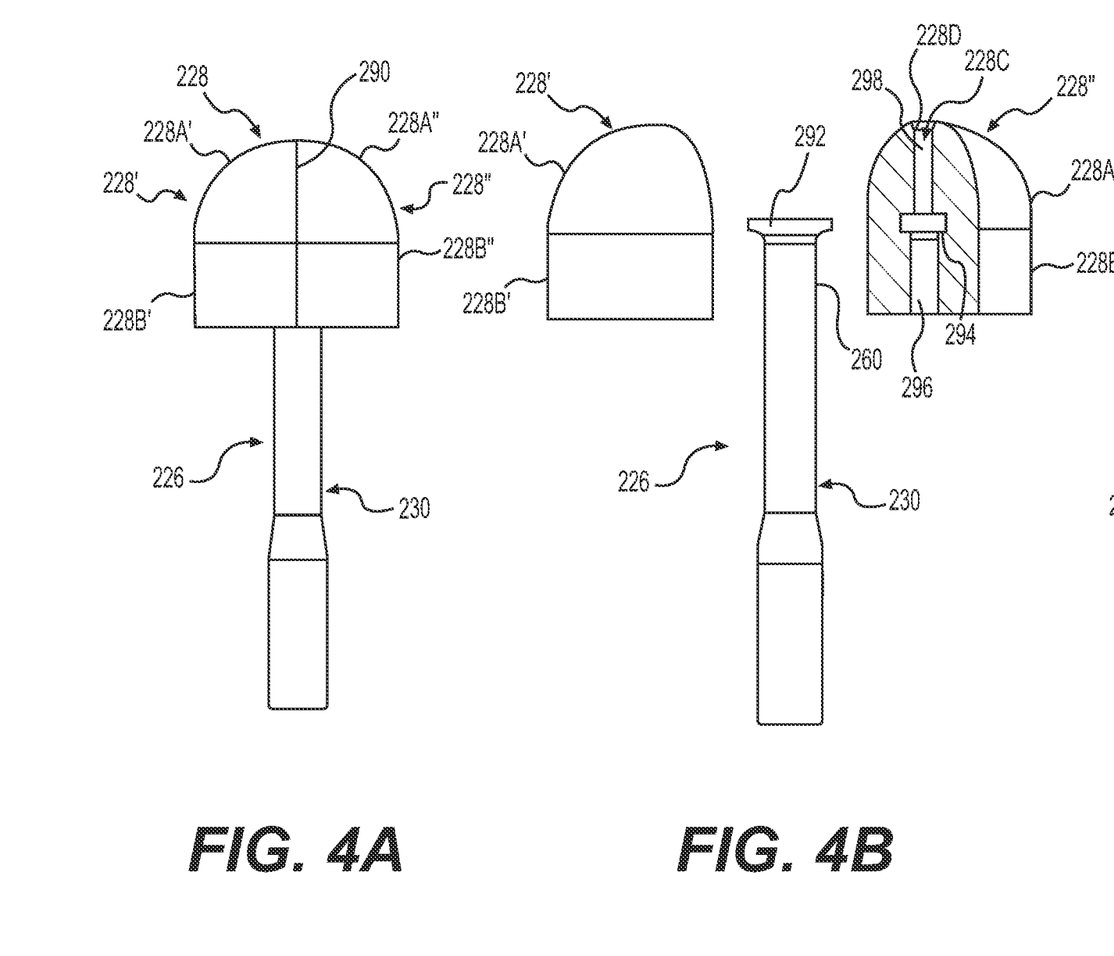
FIG. 4A illustrates a side view of a further alternative exemplary electrode portion of the medical device of FIGS. 1A and 1B, according to aspects of the present disclosure.
FIG. 4B illustrates a partially exploded view of the electrode portion of FIG. 4A.
Figure 4C:
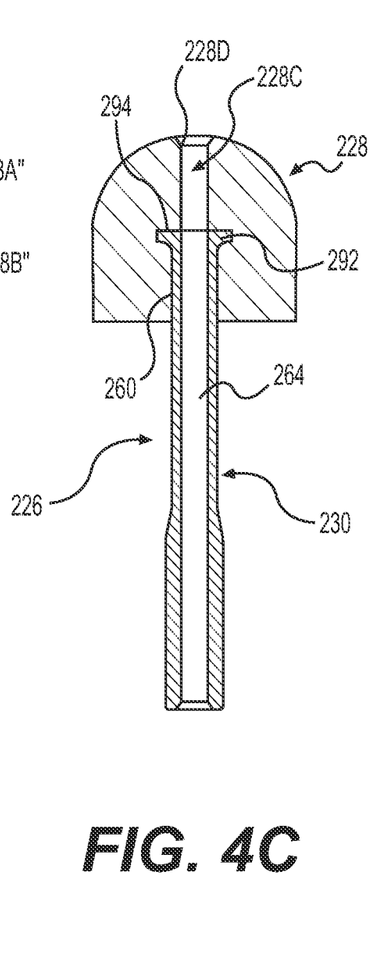
FIG. 4C illustrates a cross-sectional view of the electrode portion of FIG. 4A.

As mentioned, electrode shaft 30 may include transition portion 78, first longitudinal portion 80, and second longitudinal portion 82. In one aspect, a distal portion (e.g., first longitudinal portion 80) of electrode shaft 30 may include a consistent width. In another aspect, and as shown in FIGS. 4B and 4C, the distal end of the distal portion of electrode shaft 30 may include an increased thickness (e.g., a widened end portion 292) relative to the remaining distal portion of electrode shaft 30.

As shown in FIG. 2B, insulation tip 28 may be coupled to a distal portion of electrode shaft 30 via a solder 66. In one aspect, insulation tip 28 may include a gap 68 for example, a radial indentation or cutout, in a radial internal portion 28F of insulation tip 28. Gap 68 may occupy approximately a quarter of a longitudinal length of insulation tip 28. In this aspect, insulation tip 28 may be coupled to electrode shaft 30 by placing melted solder 66 in gap 68, and then inserting electrode shaft 30 into insulation tip 28. The solder 66 may help couple insulation tip 28 and electrode shaft 30. Additionally, as shown in FIG. 2B, radial internal portion 28F that forms insulation tip lumen 28C may transition from a wider proximal lumen (e.g., where insulation tip 28 overlaps with electrode shaft 30) to a narrower distal lumen (e.g., wherein insulation tip 28 does not overlap with electrode shaft 30). In this aspect, the transition may correspond to the distal end of gap 68, and may also help form a stop surface for the distal end face of distal tip 60 to abut internal face 28E of insulation tip 28.

Insulation tip 28 may be formed of a ceramic (e.g., zirconia, an alloy containing zirconium (e.g., $ZrO_2$), aluminum oxide ($Al_2O_3$), a ceramic alloy, etc.) a polymer material (e.g., a fluoropolymer, polyether ether ketone (PEEK), etc.) or another medically-safe, heat-resistant, and non-conductive material. Electrode shaft 30 may be formed of a conductive material, for example, a stainless steel (e.g., 316L stainless steel), titanium, or another medically-safe and conductive material. In one aspect, electrode shaft 30 may include a surface finish, for example, may be passivated per ASTM A967 Nitric 2.

Although not shown, electrode 26 may include an electrode plate. The electrode plate may be positioned at the proximal face of side portion 28B and/or may surround a portion of electrode shaft 30 just proximal to insulation tip 28. In one aspect, the electrode plate may be conductive, and may be energized when electrode shaft 30 is energized. In another aspect, the electrode plate may not be conductive. In either aspect, the electrode plate may help support insulation tip 28 and/or electrode shaft 30, and/or may help couple insulation tip 28 to electrode shaft 30.

Various portions of insulation tip 28 may include heights and width, for example, as measured relative to a longitudinal axis of insulation tip 28. Insulation tip 28 may include a width (e.g., at a proximal end of side portion 28B) of approximately 2.0 to 3.0 mm, for example, approximately 2.2 mm. Insulation tip 28 may have a height (e.g., from the proximal end of side portion 28B to a distal end face of distal end 28A) of approximately 2.0 to 3.0 mm, for example, approximately 2.1 mm. For example, distal end 28A of insulation tip 28 may be rounded (e.g., substantially hemispherical), and may include a radius of approximately 0.5 to 2.0 mm, for example, approximately 1.1 mm. Side portion 28B may have a height of approximately 0.5 to 1.0 mm, for example, approximately 0.9 mm. If electrode 26 includes the electrode plate (not shown), the electrode plate may include a height of 0.05 to 0.2 mm, for example, approximately 0.1 mm.

Additionally, as shown in FIG. 2B, the wider portion of insulation tip lumen 28C formed by radial internal portion 28F (e.g., where insulation tip 28 overlaps with electrode shaft 30) may include a height of approximately 0.5 to 1.5 mm, for example, approximately 1.0 mm, and the narrower portion of insulation tip lumen 28C (e.g., wherein insulation tip 28 does not overlap with electrode shaft 30) may include a height of approximately 0.5 to 1.5 mm, for example, approximately 1.0 mm. The wider portion of insulation tip lumen 28C formed by radial internal portion 28F (e.g., where insulation tip 28 overlaps with electrode shaft 30) may include a width of approximately 0.3 to 0.7 mm, for example, approximately 0.5 mm, and the narrower portion of insulation tip lumen 28C (e.g., wherein insulation tip 28 does not overlap with electrode shaft 30) may include a width of approximately 0.2 to 0.5 mm, for example, approximately 0.3 mm. As mentioned, distal end portion 28D may include a chamfer or angled portion, which may transition from the width of the narrowed lumen, for example, approximately 0.3 mm, to a wider width, for example, approximately 0.37 mm. In this aspect, the chamfer or angled portion of distal portion 28D may include an angle of approximately 60 degrees relative to the longitudinal axis.

Various portions of electrode shaft 30 may include heights and width, for example, as measured relative to a longitudinal axis of electrode shaft 30. Electrode shaft 30 may include a total height of approximately 4.0 to 6.0 mm, for example, approximately 5.2 mm. First longitudinal portion 80 may include a height of approximately 2.0 to 4.0 mm, for example, approximately 3.0 mm. Second longitudinal portion 82 may include a height of approximately 1.0 to 2.0 mm, for example, approximately 1.7 mm. Transition portion 78 may include a height of approximately 0.2 to 1.0 mm, for example, approximately 0.5 mm. First longitudinal portion 80 may include a width of approximately 0.4 to 0.7 mm, for example, approximately 0.5 mm. Second longitudinal portion 82 may include a width of approximately 0.5 to 0.7 mm, for example, approximately 0.6 mm. In this aspect, transition portion 78 may include an angle of approximately 7 degrees relative to the longitudinal axis. In one aspect, electrode shaft lumen 64 and insulation tip lumen 28C may be approximately the same width (e.g., in a direction transverse to the longitudinal axes of electrode shaft lumen 64 and insulation tip lumen 28C). For example, electrode shaft lumen 64 and insulation tip lumen 28C may include constant widths of approximately 0.3 mm. In this aspect, second longitudinal portion 82 may include a radial thickness (e.g., from a radial exterior to a radial interior that defines electrode shaft lumen 64) of approximately 0.5 mm, and first longitudinal portion 80 may include a radial thickness (e.g., from a radial exterior to a radial interior that defines electrode shaft lumen 64) of approximately 0.3 mm.

Figure 3A:
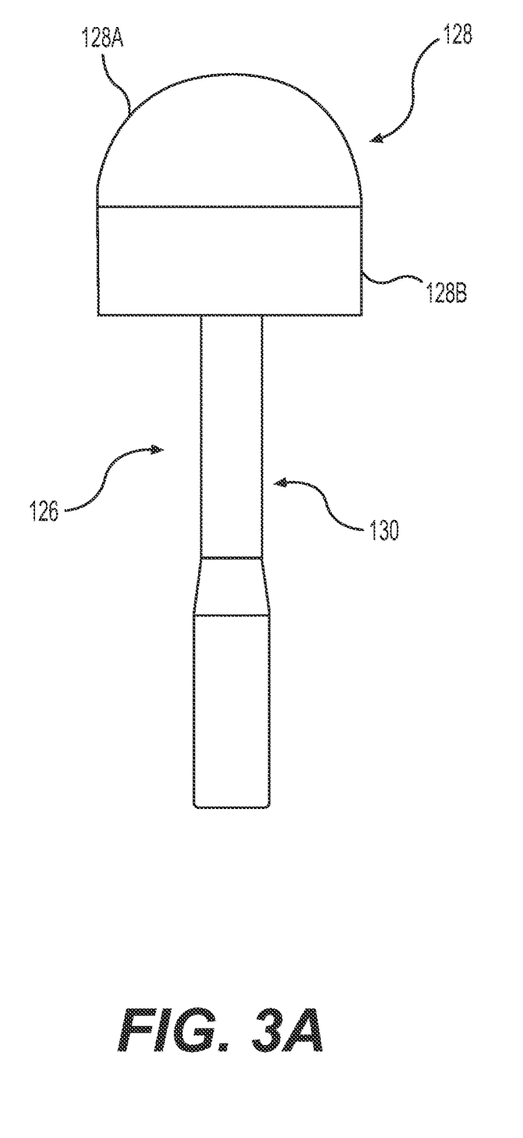
Figure 3B:
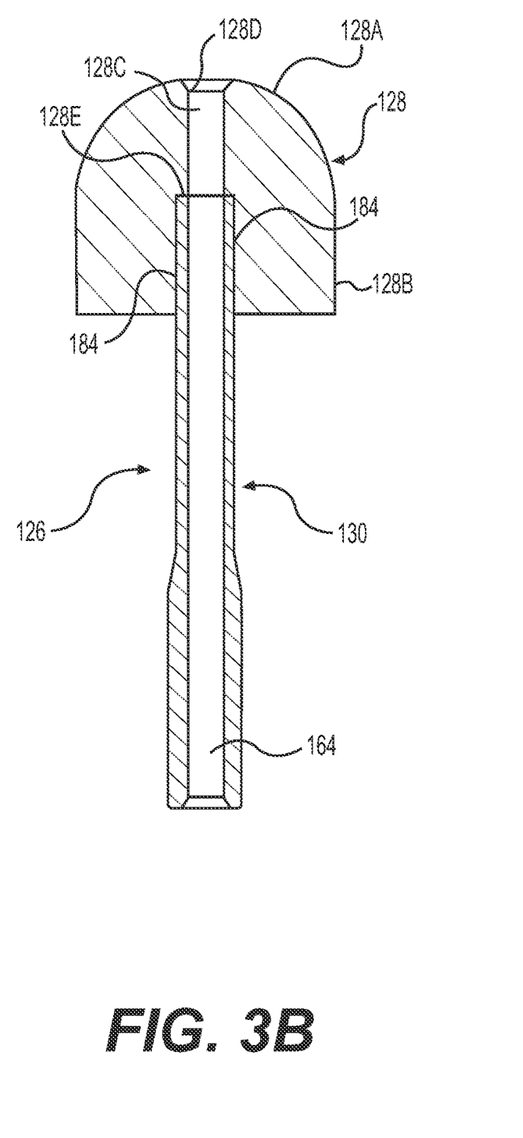
FIG. 3B illustrates a cross-sectional view of the electrode portion of FIG. 3A, according to aspects of the present disclosure.

FIGS. 3A and 3B illustrate views of another electrode 126 similar to electrode 26, with similar elements shown by 100 added to the reference numbers. As shown, electrode 126 includes an insulation tip 128 and an electrode shaft 130. Insulation tip 128 may include a distal portion 128A, which may be rounded, and a side portion 128B, which may be cylindrical. In the aspect shown in FIGS. 3A and 3B, insulation tip 128 and electrode shaft 130 may be coupled via brazing, for example, by melting and flowing (e.g., by capillary action) a filler metal (e.g., aluminum-silicon, copper, copper-silver, copper-zinc (brass), copper-tin (bronze), gold-silver, a nickel alloy, silver, an amorphous brazing foil using nickel, iron, copper, silicon, boron, phosphorous, and/or other materials) between insulation tip 128 and electrode shaft 130. Once insulation tip 128 and electrode shaft 130 are coupled, insulation tip 128 and electrode shaft 130 form a fluid channel through an electrode shaft lumen 164 and an insulation tip lumen 128C in order to deliver fluid to a target site, as discussed above. Moreover, the exposed portion of electrode shaft 130 may be energized to treat tissue, while insulation tip 128 covers and insulates the distal portion of electrode shaft 130, which may help prevent or minimize damage and/or unintended contact with tissue.

The filler metal (not shown) may have a lower melting point than the materials that form insulation tip 128 and electrode shaft 130. In one aspect, insulation tip 128 may be placed over the distal portion of electrode shaft 130 (or electrode shaft 130 may be inserted into insulation tip 128) such that electrode shaft 130 abuts internal face 128E of insulation tip 128. Then, the filler metal, which has been heated, for example, to a temperature slightly above its melting temperature (e.g., its liquidus temperature), may be flowed over the outer face of electrode shaft 130 and/or the internal face of insulation tip 128. In another example, the filler metal may be flowed over the outer face of electrode shaft 130 and/or the internal face of insulation tip 128, and then insulation tip 128 may be placed over the distal portion of electrode shaft 130 (or electrode shaft 130 may be inserted into insulation tip 128) such that electrode shaft 130 abuts internal face 128E of insulation tip 128. In the above aspects, the cooling of the filler metal helps to physically couple insulation tip 128 and electrode shaft 130.

It is noted that, in the aspects shown in FIGS. 3A and 3B, insulation tip 128 may not include a gap 68, as in insulation tip 28 of FIGS. 2A and 2B. Instead, the filler metal may couple an internal face of insulation tip lumen 28C to an outer face of electrode 130 at a junction 184. In this aspect, junction 184 (or a space between the internal face of insulation tip lumen 28C and the outer face of electrode shaft 130 that is filled by the filler material) may be approximately 0.1 mm or less, for example, approximately 0.03 to 0.08 mm.

FIGS. 4A-4C illustrate views of another electrode 226 similar to electrode 26, with similar elements shown by 200 added to the reference numbers. As shown, electrode 226 includes an insulation tip 228 and an electrode shaft 230.

Insulation tip 228 may be formed of two halves 228', 228". Half 228' may include a partially-rounded distal portion 228A' (e.g., a quarter of a sphere) and a partially cylindrical side portion 228B', and half 228" may include a partially-rounded distal portion 228A" (e.g., a quarter of a sphere) and a partially-cylindrical side portion 228B". Halves 228', 228" may be divided along a longitudinal centerline 290. For example, as shown in FIG. 4B, halves 228', 228" may be separated. Halves 228', 228" may be positioned around the distal portion (e.g., distal tip 260) of electrode shaft 230 and may be bonded or joined together, for example, via soldering (which, although not shown, may include one or more gaps to receive the solder, as discussed with respect to FIGS. 2A and 2B), brazing as discussed with respect to FIGS. 3A and 3B, welding, one or more adhesives, or any other coupling mechanism. In one aspect, joining halves 228', 228" around the distal portion of electrode shaft 230 may also couple halves 228', 228" (and thus insulation tip 228) to electrode shaft 230. Alternatively or additionally, halves 228', 228", either individually or together, may be joined to electrode shaft 230 via any of the aforementioned coupling mechanisms.

In one aspect, as shown in FIGS. 4B and 4C, the distal end of electrode shaft 230 may include widened end portion 292. Halves 228', 228" of insulation tip 228 may each include grooves 294 to receive at least a portion of widened end portion 292. For example, widened end portion 292 may be a generally cylindrical extension that extends radially outward relative to a longitudinal axis of electrode 230. In one aspect, widened end portion 292 may include a flat distal end and a curved proximal end. Halves 228', 228" of insulation tip 228 may each include a groove 294 to receive respective portions (e.g., halves) of widened end portion 292. Each groove 294 in halves 228', 228" may include a shape corresponding to the shape of widened end portion 292.

Insulation tip 228 (as formed by joined halves 228', 228") may include an insulation tip lumen 228C with a proximal portion 296 and a distal portion 298. Grooves 294 may be positioned between proximal portion 296 and distal portion 298. Proximal portion 296 may be wider than distal portion 298. As shown in FIGS. 4B and 4C, groove 294 may be wider (e.g., extend further radially away from the longitudinal axis of insulation tip 228) than proximal portion 296. Distal portion 298 may be approximately the same width as an electrode shaft lumen 264, and distal portion 298 and electrode shaft lumen 264 may form a fluid channel. Moreover, insulation tip lumen 228C may terminate distally at the distal end portion 228D, which may include a chamfer or angled portion, as mentioned above. Groove 294, proximal portion 296, and distal portion 298 may be sized to accommodate any shape or configuration of electrode 230, such that distal tip 260 is receivable into insulation tip 228. Additionally, in some aspects, portions of insulation tip 228 (e.g., groove 294 and proximal portion 296) may be sized to form a space between overlapping portions of insulation tip 228 and electrode 230, for example, to help accommodate for differences in coefficients of thermal expansion between the materials of insulation tip 228 and electrode 230.

Once insulation tip 228 and electrode shaft 230 are coupled, insulation tip 228 and electrode shaft 230 form the fluid channel through electrode shaft lumen 264 and insulation tip lumen 228C in order to deliver fluid to a target site and/or to tissue from the distal end of electrode 226, as discussed above. Moreover, the exposed portion of electrode shaft 230 may be energized to treat tissue, while insulation tip 228 covers the distal portion (e.g., distal tip 260) of electrode shaft 230, which may help prevent or minimize damage and/or unintended contact with tissue.

The electrodes, including the insulation tips and electrode shafts, help to provide a standoff or insulation between a distal portion of the electrode and tissue at the target site. Additionally, the various electrodes may help to allow for a device that may be used to both cut, dissect, ablate, mark, or otherwise treat tissue, and also deliver fluid to the target site. The fluid may be delivered to the target site distally out of the distal end of the electrode.

The various electrodes discussed herein are capable of modifying physical properties of tissue when in contact with tissue by delivering energy (e.g., radio frequency energy). The energy delivered may be monopolar or bipolar energy. The various electrodes may be coupled to a shaft, with the shaft configured to extend into a body lumen or cavity of a subject. The shaft includes an electrical element traversing the shaft and connecting the electrode to an energy source, for example, in the handle or coupled to the handle.

As discussed, the electrodes may also be coupled to an actuation member (e.g., movable body 20), for example, in the handle or coupled to the handle, that allows a user to translate the electrode relative to the shaft. The electrode may be translatable between at least a first position in which a cutting shaft (e.g., longitudinal portion 62), of the electrode is retracted within the shaft, and a second position in which the cutting shaft is extended beyond the shaft and exposed. In both the first and second positions, the distal portion that includes the insulated portions (e.g., insulation tip 28) may be extended and exposed beyond the shaft, and not retracted within the shaft. Moreover, the handle may allow for the electrodes to be positioned in one or more intermediate position (i.e., a position in which only a portion of longitudinal portion 62 is exposed).

As such, the insulated distal end face (e.g., insulation tip 28) may abut tissue and help to prevent or minimize damage or unintended contact of the electrode with the tissue. The user may also position the uninsulated electrode shaft to abut or contact tissue and apply energy to cut, dissect, ablate, mark, or otherwise treat tissue. The insulation tips may be coupled to the electrode shaft in various ways, which may allow for the insulation tip to be coupled to an existing uninsulated electrode shaft and then used in a procedure.

In one example, an electrosurgical generator coupled to the handle (or within the handle) may generate receive energy in various modes, for example, radio frequency energy in a cutting mode, a coagulation mode, etc., in order for the electrode to deliver these different modes of energy to the tissue. In one aspect, the electrosurgical generator and/or the handle may include one or more knobs, dials, buttons, etc. in order to select the energy mode. Additionally, in one example, a fluid source (e.g., a saline source) coupled to the handle may provide fluid (e.g., saline) to be delivered through the electrode to the tissue and/or the target site. The fluid may be delivered at a constant rate, a pulsed rate, a user-controlled rate, etc. In these aspects, one or more of the energy delivery and/or the fluid delivery may be controlled by one or more actuators (e.g., triggers, buttons, touch screens, foot pedals, etc.).

The medical devices and methods discussed above allow a user to treat tissue by delivering electrical energy into the tissue, and delivering fluid, either simultaneously or sequentially. For example, a user may couple an electrode to the distal end and deliver the distal end to an interior lumen of a subject to deliver medical therapy in a portion of a procedure (e.g., mark, cauterize, or resect tissue). The insulation tip may help to prevent or minimize damage and/or unintended contact between the electrode and the tissue. The user may also deliver fluid distally out of the distal end of the electrode, either simultaneously or sequentially with the energy delivered, which may help the user to more quickly and efficiently deliver the medical therapy, for example, cut, dissect, ablate, mark, coagulate, cauterize, or otherwise treat tissue. Moreover, the user may deliver fluid and energy without removing the medical device from the patient or subject, which may help to reduce the costs and duration of the procedure, also potentially reducing the risks to the subject.

While principles of the present disclosure are described herein with reference to illustrative aspects for particular applications, it should be understood that the disclosure is not limited thereto. Those having ordinary skill in the art and access to the teachings provided herein will recognize additional modifications, applications, aspects, and substitution of equivalents all fall within the scope of the aspects described herein. Accordingly, the disclosure is not to be considered as limited by the foregoing description.

We claim:

1. A medical device, comprising:
a device shaft, including a distal end and a device shaft lumen;
an electrode shaft configured to deliver energy to a treatment site and including an electrode shaft lumen configured to deliver fluid to the treatment site, wherein the electrode shaft is coupled to and longitudinally movable relative to the device shaft, and wherein the electrode shaft lumen is fluidly connected to the device shaft lumen;
an insulation tip coupled to a distal tip of the electrode shaft; and
an end cap at the distal end of the device shaft,
wherein the insulation tip includes an insulation tip lumen fluidly connected to the electrode shaft lumen and configured to deliver fluid to the treatment site,
wherein the insulation tip covers an entirety of the distal tip of the electrode shaft,
wherein the end cap includes a central opening through which the electrode shaft is movable, and wherein the end cap includes a stop surface,
wherein the electrode shaft includes a first longitudinal portion, a second longitudinal portion proximal of the first longitudinal portion, and a transition portion between the first longitudinal portion and the second longitudinal portion, and wherein the transition portion is configured to engage with the stop surface of the end cap to limit a distal extension of the electrode shaft, and
wherein the first longitudinal portion includes a cross-sectional width less than a cross-sectional width of the second longitudinal portion.

2. The medical device of claim 1, wherein the electrode shaft is formed of stainless steel, and wherein the insulation tip is formed of a ceramic or polymer material.

3. The medical device of claim 1, wherein the insulation tip overlaps longitudinally with a portion of the electrode shaft, and wherein the insulation tip is coupled to the electrode shaft via solder.

4. The medical device of claim 3, wherein a radially interior portion of the insulation tip includes a gap configured to receive at least a portion of the solder.

5. The medical device of claim 1, wherein the insulation tip overlaps longitudinally with a portion of the electrode shaft, wherein the insulation tip is coupled to the electrode shaft via brazing.

6. The medical device of claim 5, wherein, when the insulation tip is coupled to the electrode shaft, a filler material occupies a space at a junction between a portion of the electrode shaft and a portion of the insulation tip.

7. The medical device of claim 1, wherein the insulation tip includes a rounded distal end and a cylindrical side portion.

8. The medical device of claim 7, wherein the rounded distal end is hemispherical and extends distally beyond the distal tip of the electrode shaft.

9. The medical device of claim 8, wherein the insulation tip lumen includes a wide portion configured to receive a portion of the distal tip of the electrode shaft and a narrow portion extending distally beyond the distal tip of the electrode shaft.

10. The medical device of claim 9, wherein the narrow portion of the insulation tip lumen includes a cross-sectional width equal to a cross-sectional width of the electrode shaft lumen, and wherein the narrow portion includes a distal end portion that includes a chamfer.

11. The medical device of claim 10, wherein the electrode shaft lumen and the insulation tip lumen extend along a longitudinal axis of the medical device.

12. The medical device of claim 9, wherein the insulation tip includes two insulation tip halves that are coupled together to couple the insulation tip to the electrode shaft.

13. The medical device of claim 12, wherein the electrode shaft includes a widened distal portion, and wherein each of the two insulation tip halves includes a groove to receive at least a portion of the widened distal portion when the two insulation tip halves are coupled to the electrode shaft, and
wherein the groove in each of the two insulation tip halves is positioned between the wide portion of the insulation tip lumen configured to receive the portion of the distal tip of the electrode shaft and the narrow portion of the insulation tip lumen extending distally beyond the distal tip of the electrode shaft.

14. A medical device, comprising:
a device shaft, including a distal end and a device shaft lumen;
an electrode shaft configured to deliver energy to a treatment site, wherein the electrode shaft includes an electrode shaft lumen configured to deliver fluid to the treatment site, wherein the electrode shaft is coupled to and longitudinally movable relative to the device shaft, and wherein the electrode shaft lumen is fluidly connected to the device shaft lumen; and
an insulation tip coupled to a distal tip of the electrode shaft,
wherein the insulation tip includes an insulation tip lumen fluidly connected to the electrode shaft lumen and configured to deliver fluid to the treatment site,
wherein the insulation tip covers an entirety of the distal tip of the electrode shaft,
wherein the insulation tip includes a rounded distal end and a cylindrical side portion,
wherein the rounded distal end is hemispherical and extends distally beyond the distal tip of the electrode shaft,
wherein the insulation tip lumen includes a wide portion configured to receive a portion of the distal tip of the electrode shaft and a narrow portion extending distally beyond the distal tip of the electrode shaft, and
wherein the narrow portion of the insulation tip lumen includes a cross-sectional width equal to a cross-sectional width of the electrode shaft lumen, wherein the narrow portion includes a distal end portion that includes a chamfer.

15. The medical device of claim 14, wherein the electrode shaft lumen and the insulation tip lumen extend along a longitudinal axis of the medical device.

16. The medical device of claim 15, wherein the insulation tip overlaps longitudinally with a portion of the electrode shaft.

17. The medical device of claim 16, wherein the insulation tip is coupled to the electrode shaft via solder, and wherein a radially interior portion of the insulation tip includes a gap configured to receive at least a portion of the solder.

18. The medical device of claim 16, wherein the insulation tip is coupled to the electrode shaft via brazing, and wherein, when the insulation tip is coupled to the electrode shaft, a filler material occupies a space at a junction between a portion of the electrode shaft and a portion of the insulation tip.

19. A medical device, comprising:

a device shaft, including a distal end and a device shaft lumen;

an electrode shaft configured to deliver energy to a treatment site, wherein the electrode shaft includes an electrode shaft lumen configured to deliver fluid to the treatment site, wherein the electrode shaft is coupled to and longitudinally movable relative to the device shaft, and wherein the electrode shaft lumen is fluidly connected to the device shaft lumen; and an insulation tip coupled to a distal tip of the electrode shaft, wherein the insulation tip includes an insulation tip lumen fluidly connected to the electrode shaft lumen and configured to deliver fluid to the treatment site, wherein the insulation tip covers an entirety of the distal tip of the electrode shaft, wherein the insulation tip includes a rounded distal end and a cylindrical side portion, wherein the rounded distal end is hemispherical and extends distally beyond the distal tip of the electrode shaft, wherein the insulation tip lumen includes a wide portion configured to receive a portion of the distal tip of the electrode shaft and a narrow portion extending distally beyond the distal tip of the electrode shaft, wherein the insulation tip includes two insulation tip halves that are coupled together to couple the insulation tip to the electrode shaft, wherein the electrode shaft includes a widened distal portion, and wherein each of the two insulation tip halves includes a groove to receive at least a portion of the widened distal portion when the two insulation tip halves are coupled to the electrode shaft, and wherein the groove in each of the two insulation tip halves is positioned between the wide portion of the insulation tip lumen configured to receive the portion of the distal tip of the electrode shaft and the narrow portion of the insulation tip lumen extending distally beyond the distal tip of the electrode shaft.

20. The medical device of claim 19, wherein the electrode shaft is formed of stainless steel, and wherein the insulation tip is formed of a ceramic or polymer material.

* * * * *